(12) United States Patent
Budig et al.

(10) Patent No.: US 8,905,981 B2
(45) Date of Patent: Dec. 9, 2014

(54) PUMP WITH INTEGRATED CONTROL UNIT

(75) Inventors: Klaus Budig, Oelstykke (DK); Marc Anderson, Lunenburg, MA (US); Steven Vordenberg, Amherst, NH (US); James Rudolph, Nashua, NH (US); Mark Baerenrodt, Milford, NH (US); Bob Ketelhohn, Dustable, MA (US); David Carpenter, Jaffrey, NH (US)

(73) Assignee: Coloplast A/S, Humlebaek (DK)

( * ) Notice: Subject to any disclaimer, the term of this patent is extended or adjusted under 35 U.S.C. 154(b) by 329 days.

(21) Appl. No.: 13/263,339

(22) PCT Filed: Apr. 6, 2010

(86) PCT No.: PCT/DK2010/050076
§ 371 (c)(1),
(2), (4) Date: Jan. 25, 2012

(87) PCT Pub. No.: WO2010/115431
PCT Pub. Date: Oct. 14, 2010

(65) Prior Publication Data
US 2012/0130347 A1    May 24, 2012

(30) Foreign Application Priority Data

Apr. 8, 2009   (DK) ................................ 2009 00473
Aug. 14, 2009  (DK) ................................ 2009 70086
Sep. 28, 2009  (DK) ................................ 2009 70130

(51) Int. Cl.
*A61M 31/00*   (2006.01)
*A61M 3/02*    (2006.01)
*A61M 39/22*   (2006.01)
*F16K 17/04*   (2006.01)

(52) U.S. Cl.
CPC ........... *A61M 39/223* (2013.01); *A61M 3/0262* (2013.01); *A61M 3/0295* (2013.01); *F16K 17/0406* (2013.01)
USPC ...................... 604/275; 604/99.01; 604/99.02

(58) Field of Classification Search
CPC ........... A61M 1/0003; A61M 1/0009; A61M 1/0011; A61M 1/0023; A61M 1/0039; A61M 1/0066; A61M 1/0072; A61M 3/0255; A61M 3/0233; A61M 3/0254; A61M 3/0262; A61M 3/027; A61M 3/0295
USPC .............. 604/36–39, 43, 96.01, 99.01, 99.02, 604/99.04, 151, 911, 97.01, 98.01, 327, 604/328, 257, 258, 275–279
See application file for complete search history.

(56) References Cited

U.S. PATENT DOCUMENTS 4,581,014 A * 4/1986 Millerd et al. .................. 604/80
4,904,245 A * 2/1990 Chen et al. .................... 604/248

(Continued)

FOREIGN PATENT DOCUMENTS

JP       58220982      * 12/1983
WO     2004006993        1/2004
WO     2008110629        9/2008

*Primary Examiner* — Aarti B Berdichevsky
*Assistant Examiner* — Laura Schell
(74) *Attorney, Agent, or Firm* — Coloplast Corp., Coloplast A/S; Nick Baumann (57) ABSTRACT

A pump for use in anal irrigation includes a control unit integrated in the pump. The control unit includes a cylindrical housing element and a valve element fitted in the housing. The valve element and the housing element are adapted for rotating with respect to each other between a position allowing the pump to pump air into a balloon, a position allowing the pump to pump air into a reservoir bag and an evacuation position. The control unit is actuated by a handle attached to the rotatable valve element. The handle extends radially out from the rotatable valve element and the cylindrical housing.

10 Claims, 7 Drawing Sheets

(56) References Cited

U.S. PATENT DOCUMENTS 5,019,054 A * 5/1991 Clement et al. ............... 604/248
6,468,245 B2 * 10/2002 Alexandersen ............... 604/105
2003/0073974 A1 * 4/2003 Falconer ...................... 604/514
2006/0129135 A1 * 6/2006 Moeller-Jensen et al. .... 604/540
2010/0063436 A1 * 3/2010 Tanghoej et al. ............... 604/28

* cited by examiner

PUMP WITH INTEGRATED CONTROL UNIT

The invention relates to a pump with an integrated control unit for directing air either to a reservoir bag or to an inflatable balloon or evacuating the system. The invention also relates to a system for use in connection with anal irrigation.

BACKGROUND

Anal irrigation is one of a number of treatments used to aid people with bowel problems. People suffering from bowel problems are often paralyzed, typically due to spinal cord injuries, and confined to a wheelchair or hospitalized. In these situations, the peristaltic functions, i.e. the reflexes and muscles of the bowel, often cannot be stimulated correctly. This results in constipation or random discharge of bowel contents. By using anal irrigation, a stimulation of the peristaltic movements of the colon can be provided.

To perform such anal irrigation a device comprising an anal probe, also called anal catheter or speculum, is provided. The anal probe is inserted into the rectum through the anus. The anal probe is typically retained in the rectum by retention means, most commonly a balloon, which is inflated against the wall of the rectum. A liquid, such as water or a saline solution is then introduced into the rectum through the anal probe. The amount of liquid is generally below 1.5 liters, depending on the individual. The liquid is contained in a reservoir prior to use. The reservoir may for example be in the form of a canister or a reservoir bag.

The reservoir may be a pressurized bag or canister so that the liquid is displaced from the bag by pumping air into the bag. In this case, the same pump can be used to pump air into the bag and into the inflatable retention means.

DESCRIPTION OF RELATED ART

WO2004/006993A1 discloses a system for anal irrigation comprising a reservoir for irrigating liquid, a probe for arrangement in a user, and a fixation member for fixating the probe in the user. Pumping means are provided for pumping gas into the reservoir to transfer the irrigation liquid from the reservoir to the probe. The fixation member includes an inflatable cuff. The system includes a control unit that can be set in at least a cuff inflating position and a liquid transferring position.

SUMMARY OF THE INVENTION

The invention relates to a pump having an integrated control unit. When the control unit is integrated in the pump, the number of parts in the system is reduced thus making it easier to use. The control unit is provided with a handle extending radially out of the control unit. The handle makes the control unit easy to use and activate. Furthermore, the number of connections are reduced making the system more reliable and reduces the risk of error.

In the system for performing anal irrigation, the number of parts in the system is minimized. Furthermore, all valves and controls are incorporated in the most durable part—the pump. Thereby, the cost of the disposable parts is reduced.

DETAILED DESCRIPTION OF THE INVENTION

In a first aspect the invention relates to a pump for use in anal irrigation comprising
 a control unit integrated in the pump, the control unit comprising
  a cylindrical housing element and
  a valve element fitted in the housing,
   where the valve element and the housing element are adapted for rotating with respect to each other between a position allowing the pump to pump air into a balloon, a position allowing the pump to pump air into a reservoir bag and an evacuation position
  the control unit is actuated by a handle attached to the rotatable valve element
  the handle extends radially out from the rotatable valve element and the cylindrical housing This configuration of the pump and the control unit makes the control unit easy to use for people with poor hand dexterity. They are able to rotate the handle and thereby the valve element by pushing it without having to grip it by the fingers. They can use either part of their hand or the table or any other object to rotate the handle.

The handle may be attached across all of the length of the valve element that is from one side to the opposite side in the transverse direction of the pump. In other words, it may take the form of a bow extending transversely across the pump. Thereby the handle will be as long as possible making it even easier to activate. Thus the handle may be approximately 5 cm in the direction transversely across the pump. In the direction radially from the rotatable valve element, the handle may be at least approximately 2 to 3 cm. This will provide a surface area large enough to be able to easily actuate the control unit.

The pump may be in the form of a lever pump having a pivotable pump handle and a support defining a longitudinal direction of the pump, and wherein the cylindrical housing element of the control unit is transverse to the longitudinal direction of the pump.

The pump has two extreme positions, a relaxed position and a compressed position. In a relaxed position, the pump is ready to start pumping, and the pump mechanism is filled with air that can be removed upon compression of the pump mechanism. In the compressed position, (almost) all of the air has been removed from the pump mechanism. The pump handle pivots around an axis extending transverse to the longitudinal direction of the pump. In the relaxed position, the pump handle defines an angle with respect to the longitudinal direction of the pump. In the compressed position, the pump handle is substantially parallel to the longitudinal direction of the pump.

When the pump handle pivots, it actuates a pump mechanism supported by the support of the pump. The pump mechanism in the lever pump may be a bellows element, a foam element, a bulb element or a piston element. All of these pump mechanisms work well with a lever actuator (the pivotable handle). The pump mechanism as such forms no part of this invention and will not be discussed further.

The pump may be approximately 15 cm in the longitudinal direction and approximately 5 cm in the transverse direction. The pump handle may be approximately 10 cm in the longitudinal direction and extend in an angle of between 30 and 45 degrees with respect to the support, when the pump is in the relaxed position.

The pivotable pump handle may define a pivot axis of the pump and the rotatable valve element may define a rotation axis of the control unit, where the pivot axis and the rotation axis merge at one end of the pump. Thereby the handle of the control unit will extend transversely to the longitudinal direction of the pump. This configuration will provide a compact design and still leave plenty of room to operate the pump handle as well as the handle of the control unit.

The pump is adapted for use in connection with a system for performing anal irrigation. Such a system typically comprises a reservoir bag, an anal probe for inserting into the rectum, a pump for pumping liquid from the reservoir bag to the anal probe, and tubes for connecting the different parts. The anal probe is typically provided with retention means, most commonly in form of an inflatable balloon, for retaining the probe in the rectum during the irrigation procedure. A pump, as described in this invention, can be used to pump air into the retention means and to pump air into the reservoir bag so as to displace the irrigation liquid contained in the bag. Thus the pump is connected to a balloon tube leading air from the pump to the balloon and to a reservoir tube leading air from the pump to the reservoir bag. Furthermore, the reservoir bag and the probe are connected through a liquid tube.

The cylindrical housing may include an air inlet for leading air into the control unit and outlets for leading air out of the control unit. A balloon outlet leads air to a connection for a balloon tube, a reservoir outlet leads air to a connection for a reservoir tube and an evacuation outlet leads air to the ambience.

The valve element includes channels for directing the air between the inlet and the different outlets of the housing. A balloon channel connects the inlet and the balloon outlet, a reservoir channel connects the inlet and the reservoir outlet and a third channel connects the inlet and the evacuation outlet.

The control unit can be set in three positions where the first position is a balloon inflation position, the second position is a reservoir pumping position and the third position is an air evacuation position. In an embodiment, the first position also allows for depressurizing the bag. This provides for a flow stop for the liquid travelling through the system. Thereby the user is able to stop the irrigation procedure and re-start it if desired. One way of allowing depressurizing the bag is to provide the control unit with a valve, which is activated in the first position.

In an embodiment the control unit comprises a spring valve element. This spring valve element functions as a release valve for the reservoir bag. In case the pressure in the bag exceeds the resistance of the spring, the spring valve opens and leads the excess pressure out of the control unit and to the ambience. Thereby, the bag is prevented from bursting due to overpressure and from delivering water too fast into the intestines. The spring valve will be set to release the pressure at approximately 200 mBar±5 mBar.

In an embodiment, the pump may be provided with a stop for indicating the first position for the handle and thereby the control unit.

In a second aspect the invention relates to a system for use in anal irrigation comprising
 a reservoir bag including irrigation liquid,
 an anal probe including inflatable retention means,
 a pump for pumping air into the retention means and into the reservoir bag so as to displace the liquid from the bag,
 a control unit integrated in the pump for shifting between pumping air into the retention means, the reservoir bag and evacuating the system,
 an overpressure valve integrated in the pump for releasing the pressure in the system in case of overpressure.
 a first air tube for connecting the pump with the anal probe,
 a second air tube for connecting the pump with the reservoir bag, and
 a liquid tube for connecting the reservoir bag with the anal probe.

A system as the one described above only consists of a few parts and is thus easier to understand and use than a more complex system. In the system, the pump is intended to be re-used for the longest period of time, for example up to six months. The reservoir bag is intended to be re-used for a few months, for example two months, while the remaining parts are intended to be replaced more frequently. The probe is thus intended for one-time use only. In this system, all valves of the system are placed in the most durable part (the pump) so as to reduce cost of the parts that are more frequently disposed of.

The system includes an anal probe for inserting into the rectum. The probe has a tip part and a connector part and there between a cylindrical body. The diameter of the cylindrical body is about 8-16 mm, for example 10 mm. The length of the body is about 70-200 mm, for example about 150 mm. The anal probe is typically provided with a coating on the outer surface to make insertion easier. Furthermore, the probe is typically provided with retention means on the outer surface, for example in form of a balloon. The tip part is provided with eyelets for letting liquid out of the probe. The connector part is provided with two inlets. The probe includes two channels, an air channel extending from the connector part to the surface of the probe under the balloon, and a liquid channel extending from the connector part to the tip part to communicate with the eyelets.

The system also includes a pump for pumping air into the reservoir bag and into the retention means on the probe. Such a pump is connected to two air tubes—one for leading air from the pump to the probe and one for leading air from the pump to the reservoir bag. The pump may be a pump as described above.

The reservoir bag contains the irrigation liquid. The liquid will typically be in the form of tap water. The reservoir bag is a bag adapted for withstanding pressure. The bag can be made of Low-Density-Polyethylene (LDPE) and will typically be welded at its side. The reservoir bag is provided with an inlet placed in the top of the bag, the inlet of which can be closed with a lid. The inlet comprises a fitting for a connector so that tubes can be attached to the bag.

The system further includes two connectors for connecting the anal probe and the reservoir bag to the tubes in the system. Finally, two air tubes and one liquid tube is provided. The liquid tube extends from the reservoir bag and to the anal probe.

To prepare the system for use, the user fills the reservoir bag with tap water and closes the lid on the bag. Then one of the connectors, including an air tube and the liquid tube, is attached to the bag. The other end of this air tube is attached to the pump. Another air tube is attached to the pump in one end—this air tube terminates in the other connector including the other end of the liquid tube. This connector is then attached to the anal probe. Now the system is ready to use.

To begin using the system, the user inserts the anal probe in the rectum and pumps air into the retention means. When the anal probe is able to support itself in the rectum, the user can begin to pump air into the reservoir bag. The pressure built up in the reservoir bag will eventually displace the liquid from the bag, through the liquid tube and the anal probe and further into the rectum. After enough water has been entered into the rectum, the user evacuates the air from the system, thereby deflating the retention means and removing the pressure from the bag. Now the anal probe can be removed from the rectum and the system can be dismantled again. The probe is disposed of after use.

DETAILED DESCRIPTION OF THE DRAWING

Figure 1:
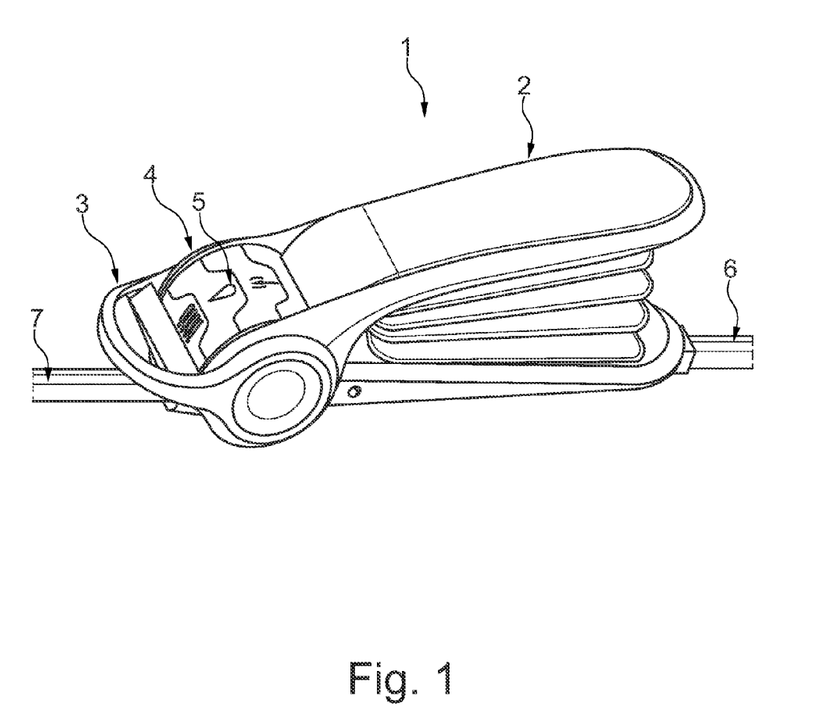
FIG. 1 illustrates a pump including a control unit according to the invention.

FIG. 1 illustrates a pump 1 including a control unit according to the invention. The pump 1 is provided with a pump handle 2 for operating the pump mechanism inside the pump. The pump mechanism is shown as a bellows pump and will not be discussed in more detail. The pump 1 is also provided with a handle 3 for operating the control unit 4. Furthermore, the pump 1 of this embodiment includes pictograms 5 illustrating the different positions of the handle 3. The pump 1 is connected to a first air channel 6 leading to the balloon and a second air channel 7 leading to the reservoir bag.

Figure 2A:
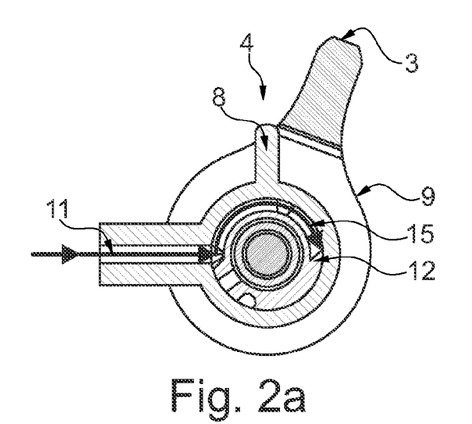
FIGS. 2a-2c illustrate a schematic drawing of the pump in a balloon-inflating position.
Figure 2B:
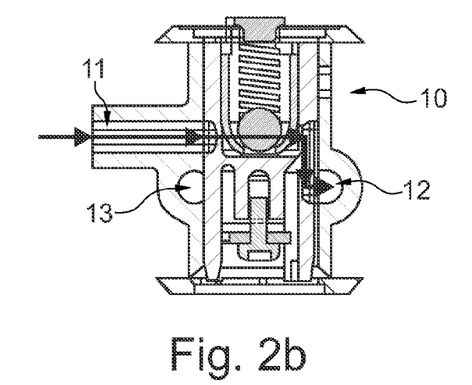
Figure 2C:
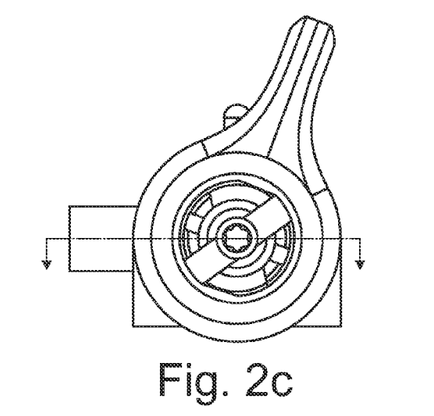

FIGS. 2a-2c illustrate the control unit 4 in a first position, that is a balloon inflating position. FIG. 2a illustrates a cross-sectional view of the control unit seen from the side. FIG. 2b illustrates a cross-sectional view of the control unit seen from the top, and FIG. 2c illustrates a side view. The control unit 4 may be provided with a stop 8 for indicating the first position. The control unit 4 comprises a cylindrical housing element 9 and a valve element 10, where the housing 9 is rotatable around the cylinder axis of the housing. The valve element 10 comprises an inlet 11 for the air being supplied from the pump mechanism (not shown). The valve element 10 comprises two outlets 12, 13 for leading air out of the valve element. The first outlet 12 is the balloon outlet and the second outlet 13 is the reservoir bag outlet. The valve element 10 also comprises air evacuation outlets 14a and 14b (FIGS. 4c, 4d). The outlets of the valve element are all connected to the inlet through channels. The balloon outlet 12 is connected to the inlet 11 through a balloon channel 15 (FIG. 2a), the reservoir bag outlet 13 is connected to the inlet 11 through a reservoir channel 16 (FIG. 3a) and the evacuation outlet is connected to the inlet through evacuation channels 17a and 17b (FIGS. 4c, 4d).

Figure 3A:
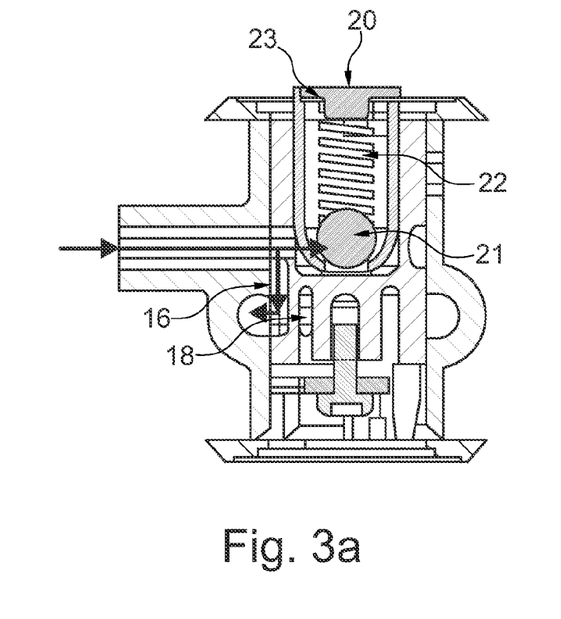
FIGS. 3a-3d illustrate the pump in a reservoir bag position.
Figure 3B:
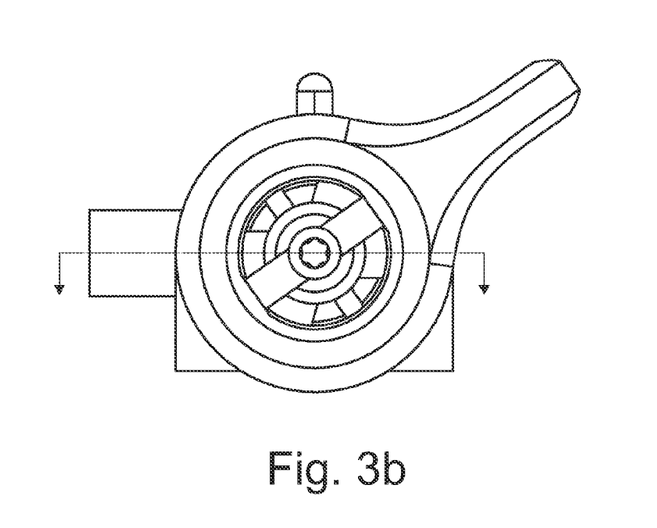
Figure 3C:
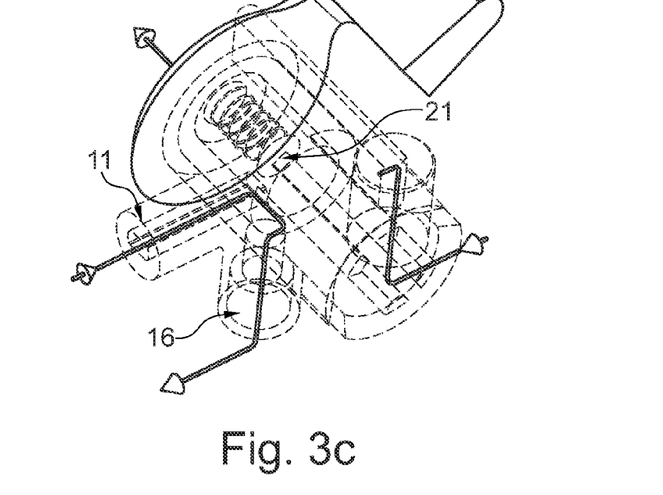
Figure 3D:
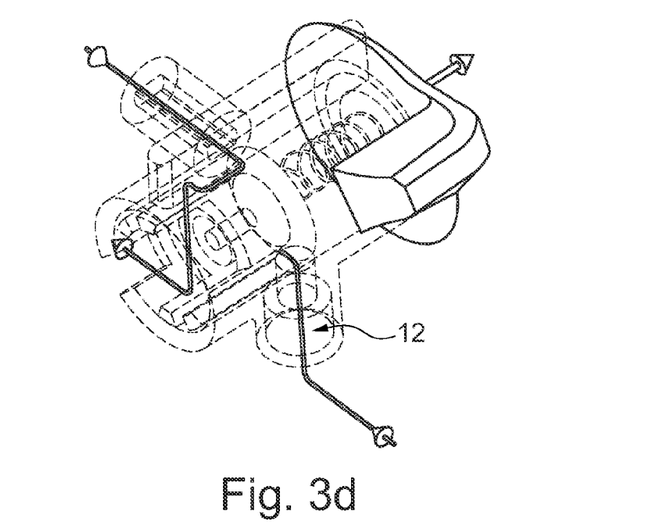

FIGS. 3a and 3b illustrate views corresponding to FIGS. 2b and 2c of the control unit 4 in a second position, a reservoir bag pumping position. FIGS. 3c and 3d illustrate perspective views of the control unit 4 in the same position. As it appears from FIG. 3a, the housing element 9 is provided with stops 18 for blocking the channels 15, 16, 17 in different positions.

The valve element 10 also comprises a release valve 20 for releasing the pressure in the system, if the reservoir bag is subjected to overpressure. The release valve 20 comprises a ball valve 21 attached to a spring 22 which in turn is attached to a stopper 23 for blocking an outlet. When the pressure in the reservoir channel 16 exceeds the pressure exerted on the ball valve 21 by the spring 22, then the spring 22 will collapse slightly and thereby open the stopper 23. This way the pressure can be released to the ambience.

In FIGS. 3c and 3d the different air-flows through the control unit 4 are illustrated. Air flows into the control unit 4 through the inlet channel 11. From the inlet channel 11 the air flows in towards the ball valve 21 and further out through the reservoir channel 16. If the pressure gets too high, excess pressure is released axially out of the control unit 4 as indicated by the arrow extending axially out. In FIG. 3d it is illustrated that the air in the system coming from the balloon will be kept enclosed, as there is no pathway through the control unit 4 when the unit is in its second position. The air from the balloon will be stopped after the balloon outlet 12. Thereby, the pressure in the balloon will be maintained in this position of the control unit.

Figure 4A:
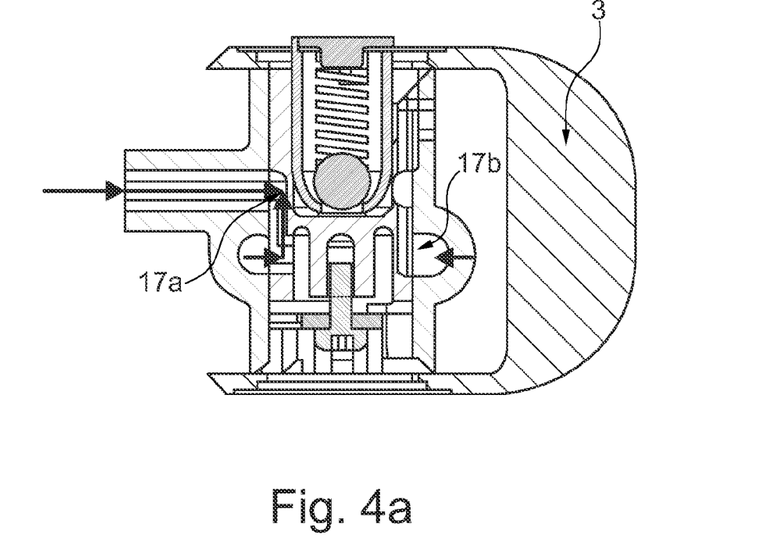
FIGS. 4a-4d illustrate the pump in an air evacuation position.
Figure 4B:
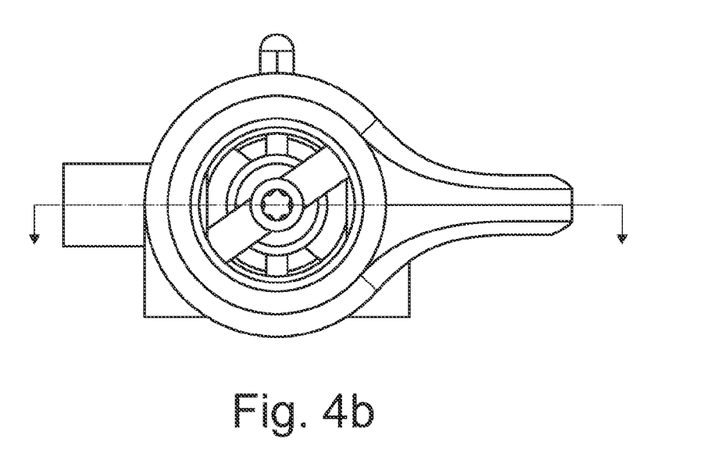
Figure 4C:
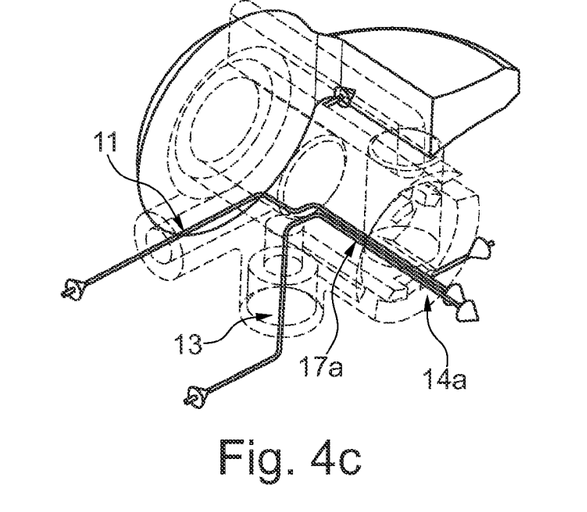
Figure 4D:
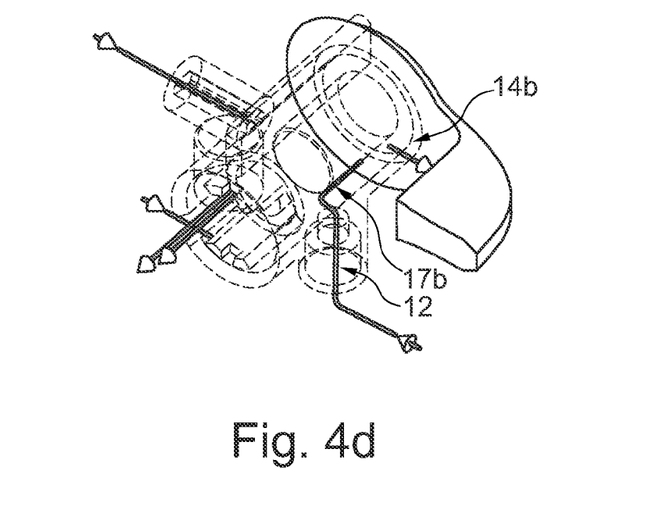

FIGS. 4a and 4b illustrate views corresponding to FIGS. 2b and 2c of the control unit 4 in a third position, that is an air evacuation position. FIGS. 4c and 4d illustrate perspective views of the control unit 4 in the same position. In FIGS. 4c and 4d it can be seen that air coming from the pump through inlet 11 and air coming from the reservoir bag through reservoir bag outlet 13 is evacuated through air evacuation channel 17a and through evacuation outlet 14a. Air coming from the balloon through balloon outlet 12 is evacuated through air evacuation channel 17b and through evacuation outlet 14b.

Figure 5:
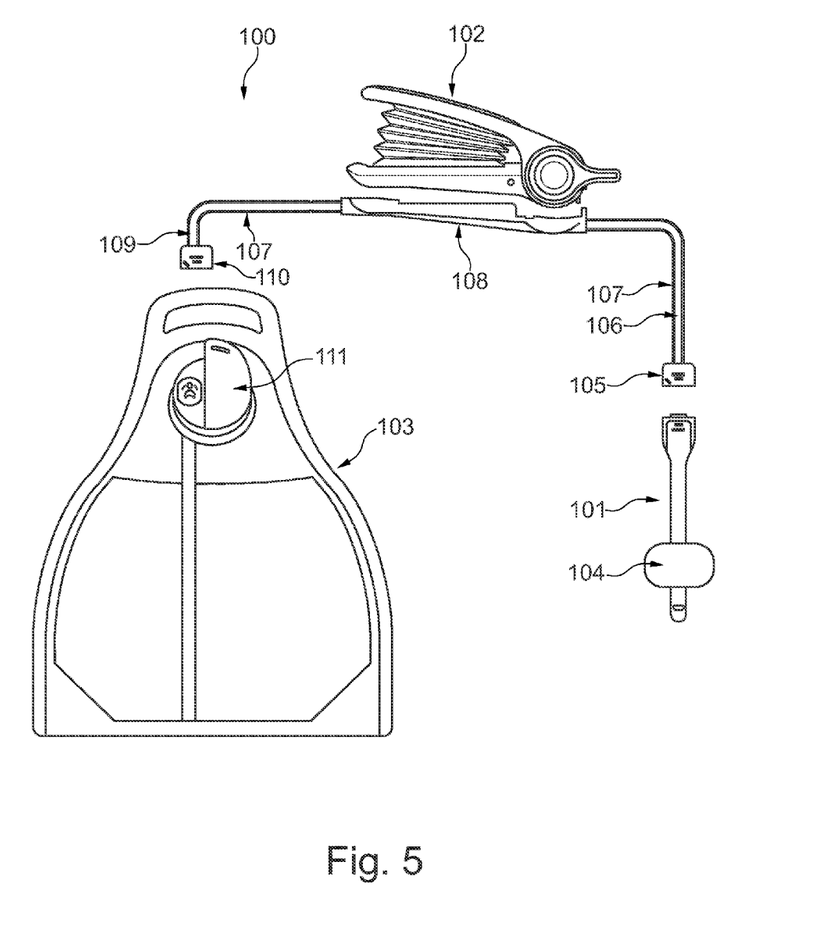
FIG. 5 illustrates a system according to another aspect of the invention.

In FIG. 5 a system 100 according to the invention is illustrated. The system 100 comprises an anal probe 101, a pump 102 and a reservoir bag 103. The probe is provided with retention means 104 in form of a balloon element. A connector 105 connects the probe 101 with a first air tube 106 for providing air from the pump 102 and a liquid tube 107 for providing liquid from the reservoir bag 103. The pump 102 is connected to the tubes through a cassette 108 including the through-going liquid tube 107 and two inlets for first and second air tubes 106, 109. The pump 102 is provided with outlets corresponding to the inlets. The second air tube 109 provides air from the pump 102 to the reservoir bag 103. A second connector 110 connects the second air tube 109 and the liquid tube 107 to the cap 111 at the reservoir bag. All valves for directing the air to the different tubes, for evacuating the system and an overpressure valve are placed in the pump, which is the most durable part of the system. In this embodiment the pump 102 can be of the kind described in connection with FIGS. 1-4.

The invention claimed is:

1. An anal irrigation system comprising:
   a control unit integrated into a pump, the control unit comprising
   a cylindrical housing element and
   a valve element fitted inside and extending between opposite ends of the cylindrical housing element,
      where the valve element and the cylindrical housing element are adapted for rotating with respect to each other between a position allowing the pump to pump air into a balloon, a position allowing the pump to pump air into a reservoir bag, and an evacuation position;
   a pump handle attached to the cylindrical housing element;
   a control unit handle attached to the valve element at opposite ends of a longitudinal length of the cylindrical housing element;
   wherein the control unit handle extends radially out from the valve element; and
   wherein the pump handle defines a pivot axis of the pump and the valve element defines a rotation axis of the control unit, and the pivot axis and the rotation axis coincide.

2. The system according to claim 1, wherein the pump is a lever pump having a pivotable pump handle and a support defining a longitudinal direction of the pump.

3. The system according to claim 1, wherein the control unit includes an air inlet for leading air from the pump mechanism to the control unit, a balloon outlet for leading air to a tube connected to a balloon, a reservoir outlet for leading air into a tube connected to a reservoir, and an evacuation outlet for leading air into the ambience.

4. The system according to claim 1, wherein the valve element comprises channels connecting an inlet with different outlets.

5. The system according to claim 4, wherein the housing element comprises stops for selectively blocking the channels.

6. The system according to claim 1, wherein the valve element further includes a spring release valve adapted for releasing over pressure from the reservoir bag.

7. The system according to claim 1, wherein the control unit includes three positions, a balloon inflating position, a reservoir bag position and an air evacuation position.

8. The system according to claim 7, wherein the balloon inflating position is adapted for evacuation air from the reservoir bag so as to function as a flow stopper.

9. The system according to claim 1, further comprising
a reservoir bag including irrigation liquid,
an anal probe including inflatable retention means,
a first air tube for connecting the pump with the anal probe,
a second air tube for connecting the pump with the reservoir bag, and
a liquid tube for connecting the reservoir bag with the anal probe.

10. The system according to claim 1, wherein the control unit handle spans over an entirety of the rotatable valve element and the cylindrical housing element.

* * * * *